United States Patent [19]

Maurer et al.

[11] 4,093,718
[45] * June 6, 1978

[54] O,O-DIALKYL-5-HALO-PYRIMIDIN(2) YL-THIONOPHOSPHORIC ACID ESTERS

[75] Inventors: Fritz Maurer; Hans-Jochem Riebel, both of Wuppertal; Ingeborg Hammann, Cologne; Wolfgang Behrenz, Overath-Steinenbrueck; Bernhard Homeyer, Opladen, all of Germany

[73] Assignee: Bayer Aktiengesellschaft, Leverkusen, Germany

[*] Notice: The portion of the term of this patent subsequent to Mar. 29, 1994, has been disclaimed.

[21] Appl. No.: 656,041

[22] Filed: Feb. 6, 1976

[30] Foreign Application Priority Data

Feb. 22, 1975 Germany ............................ 2507702

[51] Int. Cl.$^2$ ........................... A01N 9/36; C07F 9/56
[52] U.S. Cl. .................................... 424/200; 544/243; 544/315
[58] Field of Search ..................... 260/251 P; 424/200

[56] References Cited

U.S. PATENT DOCUMENTS

| 3,741,968 | 6/1973 | Haubein ............................ 260/251 P |
| 3,981,993 | 9/1976 | Maurer et al. ...................... 424/200 |
| 4,014,996 | 3/1977 | Maurer et al. ...................... 424/200 |
| 4,053,594 | 10/1977 | Riebel et al. ...................... 424/200 |

FOREIGN PATENT DOCUMENTS 300,740  10/1954  Switzerland.

Primary Examiner—Donald G. Daus
Assistant Examiner—Diana G. Rivers
Attorney, Agent, or Firm—Burgess, Dinklage & Sprung

[57] ABSTRACT

O,O-Dialkyl-5-halo-pyrimidin(2)yl-thionophosphoric acid esters of the formula

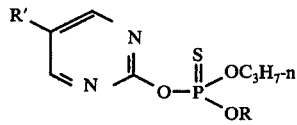

in which
R is methyl or ethyl and
R' is halogen,
which possess insecticidal and acaricidal properties.

8 Claims, No Drawings

O,O-DIALKYL-5-HALO-PYRIMIDIN(2) YL-THIONOPHOSPHORIC ACID ESTERS

The present invention relates to and has for its objects the provision of particular new O,O-dialkyl-5-halo-pyrimidin(2)yl-thionophosphoric acid esters, which possess insecticidal and acaricidal properties, active compositions in the form of mixtures of such compounds with solid and liquid dispersible carrier vehicles, and methods for producing such compounds and for using such compounds in a new way especially for combatting pests, e.g. insects and acarids, with other and further objects becoming apparent from a study of the within specification and accompanying examples.

It is known from U.S. Pat. Nos. 3,741,968 and 2,754,243 that pyrimidinylthionophosphoric acid esters, for example O,O-dimethyl-(Compound A) or O,O-diethyl-O-pyrimidin(2)yl-(Compound B) and O,O-diethyl-O-[2-isopropyl-4-methyl-pyrimidin(6)yl]-thionophosphoric acid esters (Compound C), possess insecticidal and acaricidal properties.

The present invention provides the pyrimidin(2)yl-thionophosphoric acid esters of the general formula

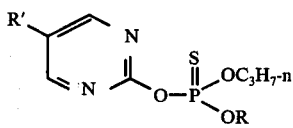

in which
R is methyl or ethyl and
R' is halogen, preferably chlorine or bromine.

Surprisingly, the pyrimidin(2)yl-thionophosphoric acid esters of the formula (I), according to the invention, are distinguished by a better insecticidal, including soil-insecticidal, and acaricidal action than the corresponding compounds of analogous structure and of the same type of action, previously known from the state of the art. The products according to the present invention thus represent a genuine enrichment of the art.

The present invention also provides a process for the preparation of a pyrimidin(2)yl-thionophosphoric acid ester of the formula (I) in which an O,O-dialkylthionophosphoric acid diester halide of the general formula

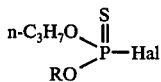

in which
R has the above-mentioned meaning and
Hal is halogen, preferably chlorine, is reacted with a 2-hydroxypyrimidine of the general formula

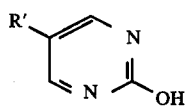

in which
R' has the above-mentioned meaning, the 2-hydroxypyrimidine being employed as such, in the presence of an acid acceptor, or in the form of an alkali metal salt, alkaline earth metal salt or ammonium salt thereof.

If, for example, O-n-propyl-O-ethyl-thionophosphoric acid diester chloride and 2-hydroxy-5-fluoropyrimidine are used as starting materials, the course of the reaction can be represented by the following equation:

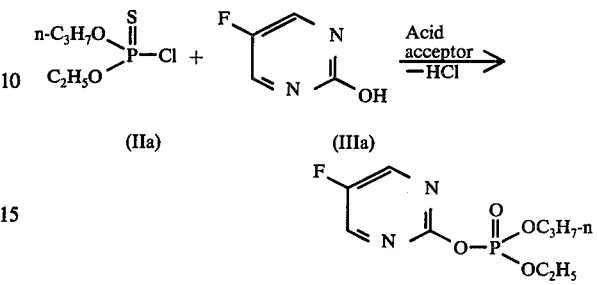

The O,O-dialkylthionophosphoric acid diester halides (II) are described in the literature and are obtainable in accordance with customary processes. The 2-hydroxypyrimidine derivatives (III) can be obtained by reacting the hydrochloride of 2-hydroxypyrimidine, which is prepared from 1,1,3,3-tetramethoxypropane and urea in alcoholic solution by treatment with hydrogen chloride according to U.S. Pat. No. 3,741,968, with elementary halogen in aqueous solution, in accordance with the following equation:

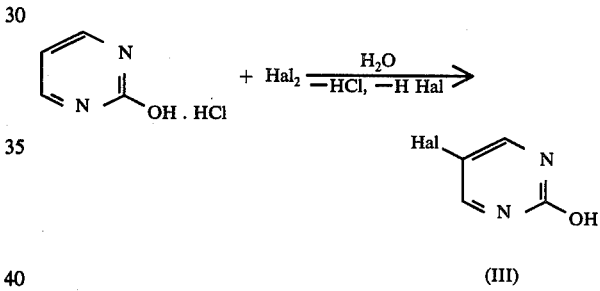

The following may be mentioned as examples of the 2-hydroxypyrimidine derivatives (III) to be employed: 2-hydroxy-5-fluoro-pyrimidine, -5-chloro-pyrimidine, -5-bromo-pyrimidine and -5-iodo-pyrimidine.

The preparative process is preferably carried out in the presence of a suitable solvent and diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as the acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 10° and 100° C, preferably at from 35° to 60° C.

The reaction is in general allowed to take place under normal pressure.

To carry out the process, the starting materials are in general employed in equimolar amounts. An excess of one or the other reactant in general produces no significant advantages. The reaction is preferably carried out in the presence of one of the above-mentioned solvents, if appropriate in the presence of an acid acceptor, at the stated temperatures. After a reaction time of one or more hours, in most cases at elevated temperature, the batch is cooled and the reaction mixture is poured into water and taken up in an organic solvent, for example toluene. Thereafter, the reaction mixture is worked up in the usual manner by drying the organic phase and evaporating the solvent.

The new compounds are obtained in the form of oils, which cannot be distilled without decomposition but can be freed from the last volatile constituents by so-called "slight distillation", that is to say prolonged heating under reduced pressure to moderately elevated temperatures, and can be purified in this way. They are characterized by the refractive index.

As already mentioned, the pyrimidin(2)yl-thionophosphoric acid esters according to the invention are distinguished by an excellent insecticidal, including soil-insecticidal, and acaricidal activity. They are active against plant pests, pests harmful to health and pests of stored products and combine a low phytotoxicity with a good action against both sucking and biting insects and against mites, and in part also against nematodes.

For this reason, the compounds according to the invention can be employed successfully as pesticides in plant protection and also in the hygiene field and the field of protection of stored products.

The active compounds according to the invention are well tolerated by plants and have a favorable level of toxicity to warm-blooded animals, and can be used for combating all or individual stages of development, including the pre-embryonic, normally sensitive and resistant, stages of development of insects and acarids where these are known as pests in agriculture, in forestry, in the protection of stored products and materials, and in hygiene.

The economically important pests in agriculture and forestry, as well as pests of stored products, pests destructive of materials and pests harmful to health, include: from the order of the Acarina, for example, *Acarus siro, Argas reflexus, Ornithodoros moubata, Dermanyssus gallinae, Eriophyes ribis, Phyllocoptruta oleivora, Boophilus microplus, Rhipicephalus evertsi, Sarcoptes scabiei,* Tarsonemus spec., *Bryobia praetiosa, Panonychus citri, Panonychus ulmi, Tetranychus tumidus* and *Tetranychus urticae;* from the order of the Thysanura, for example, *Lepisma saccharina;* from the order of the Collembola, for example, *Onychiurus armatus;* from the order of the Orthoptera, for example, *Blatta orientalis, Periplaneta americana, Leucophaea maderae, Blattella germanica, Acheta domesticus,* Gryllotalpa spec., *Locusta migratoria migratorioides, Melanoplus differentialis* and *Schistocerca gregaria;* from the order of the Dermaptera, for example, *Forficula auricularia;* from the order of the Isoptera, for example, Reticulitermes spec.; from the order of the Anoplura, for example, *Phylloxera vastatrix,* Pemphigus spec. and *Pediculus humanus corporis;* from the order of the Thysanoptera, for example, *Hercinothrips femoralis* and *Thrips tabaci;* from the order of the Heteroptera, for example, Eurygaster spec., *Dysdercus intermedius, Piesma quadrata, Cimex lectularius, Rhodnius prolixus* and Triatoma spec.; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi,* Empoasca spec., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spec., and Psylla spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spec., *Bucculatrix thurberiella, Phyllocnistis citrella,* Agrotis spec., Euxoa spec., Feltia spec., *Earias insulana,* Heliothis spec., *Laphygma exigua, Mamestra brassicae, Panolis flammea, Prodenia litura,* Spodoptera spec., *Trichoplusia ni, Carpocapsa pomonella,* Pieris spec., Chilo spec., *Pyrausta nubilalis, Ephestia kuhniella, Galleria mellonella, Cacoecia podana, Capua reticulana, Choristoneura fumifernana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spec., *Psylliodes chrysocephala, Epilachna varivestis,* Atomaria spec., *Oryzaephilus surinamensis,* Anthonomus spec., Sitophilus spec., *Otiorrhynchus sulcatus, Cosmopolites sordidus, Ceuthorrhynchus assimilis, Hypera postica,* Dermestes spec., Trogoderma spec., Anthrenus spec., Attagenus spec., Lyctus spec., Meligethes aeneus, Ptinus spec., Niptus hololeucus, Gibbium psylloides, Tribolium spec., Tenebrio molitor, Agriotes spec., Conoderus spec., *Melolontha melolontha, Amphimallus solstitialis* and *Costelytra zealandica;* from the order of the Hymenoptera, for example, Diprion spec., Hoplocampa spec., Lasius spec., *Monomorium pharaonis* and Vespa spec.; from the order of the Diptera, for example, Aëdes spec., Anopheles spec., Culex spec., *Drosophila melanogaster, Musca domestica,* Fannia spec., *Stomoxys calcitrans,* Hypoderma spec., *Bibio hortulanus, Oscinella frit,* Phorbia spec., *Pegomyia hyoscyami, Calliphora erythrocephala,* Lucilia spec., Chrysomyia spec., *Ceratitis capitata, Dacus oleae* and *Tipula paludosa;* and from the order of the Siphonaptera, for example, *Xenopsylla cheopis.*

When used against pests harmful to health and pests of stored products, the active compounds are distinguished by an excellent residual action on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ethers, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, dusting agents, foams, granules, aerosols, capsules in polymeric substances and in coating compositions, formulations for use with burning equipment such as fumigating cartridges, cans and coils, and the like.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combatting or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier, and the concentrate was diluted with water to the desired concentration.

1 $cm^3$ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following table:

Table 1
(Drosophila test)

| Active compound | | Active compound concentration in % | Degree of destruction in % after 1 day |
|---|---|---|---|
| (structure: pyrazine-O-P(=S)(OCH₃)(OCH₃)) (known) | (A) | 0.001<br>0.0001 | 100<br>0 |
| (structure: Cl-pyrazine-O-P(=S)(OC₃H₇-n)(OCH₃)) | (4) | 0.001<br>0.0001 | 100<br>100 |
| (structure: Cl-pyrazine-O-P(=S)(OC₃H₇-n)(OC₂H₅)) | (3) | 0.001<br>0.0001 | 100<br>100 |

EXAMPLE 2

Laphygma test
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cotton leaves (Gossypium hirsutum) were sprayed with the preparation of the active compound until dew-moist and were then infested with caterpillars of the owlet moth (Laphygma exigua).

After the specified periods of time, the destruction in % was determined. 100% means that all caterpillars had been killed whereas 0% indicates that no caterpillars had been killed.

The active compounds, the concentrations of the active compound, the evaluation times and the results can be seen from the following table:

Table 2
(Laphygma test)

| Active compound | | Active compound concentration in % | Degree of destruction in % after 3 days |
|---|---|---|---|
| (structure: pyrazine-O-P(=S)(OCH₃)(OCH₃)) (known) | (A) | 0.01<br>0.001 | 100<br>0 |
| (structure: Br-pyrazine-O-P(=S)(OC₂H₅)(OC₃H₇-n)) | (1) | 0.01<br>0.001 | 100<br>100 |

EXAMPLE 3

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamond-back moth (Plutella maculipennis).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 3
(Plutella test)

| Active compound | | Active compound concentration in % | Degree of destruction in % after 3 days |
|---|---|---|---|
| (structure: pyrazine-O-P(=S)(OC₂H₅)(OC₂H₅)) (known) | (B) | 0.01<br>0.001 | 100<br>0 |
| (structure: Cl-pyrazine-O-P(=S)(OC₃H₇-n)(OC₂H₅)) | (4) | 0.01<br>0.001 | 100<br>95 |
| (structure: Br-pyrazine-O-P(=S)(OCH₃)(OC₃H₇-n)) | (2) | 0.01<br>0.001 | 100<br>100 |
| (structure: Br-pyrazine-O-P(=S)(OC₂H₅)(OC₃H₇-n)) | (1) | 0.01<br>0.001 | 100<br>100 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 4

| (Tetranychus test | | |
| Active compound | Active compound concentration in % | Degree of destruction in % after 2 days |
| --- | --- | --- |
| $\overset{S}{\underset{O-P(OC_2H_5)_2}{\parallel}}$ structure, CH$_3$–N=...=N–CH(CH$_3$)$_2$ (known) (C) | 0.1 0.01 | 95 0 |
| Cl–CH=CH–N=...–N structure with O–P(=S)(OC$_3$H$_7$-n)(OCH$_3$) (4) | 0.1 0.01 | 100 99 |
| Cl–CH=CH–N=...–N structure with O–P(=S)(OC$_3$H$_7$-n)(OC$_2$H$_5$) (3) | 0.1 0.01 | 100 60 |
| Br–CH=CH–N=...–N structure with O–P(=S)(OCH$_3$)(OC$_3$H$_7$-n) (2) | 0.1 0.01 | 100 95 |
| Br–CH=CH–N=...–N structure with O–P(=S)(OC$_2$H$_5$)(OC$_3$H$_7$-n) (1) | 0.1 0.01 | 100 98 |

EXAMPLE 5

Critical concentration test/soil insects
Test insect: *Phorbia antiqua* — grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all test insects had been killed and was 0% if exactly as many test insects were still alive as in the case of the untreated control.

The active compounds, amounts used and results can be seen from the table which follows:

Table 5

| Soil insecticide test (*Phorbia antiqua* - grubs in the soil) | |
| Active compound | Degree of destruction in % at an active compound concentration of 5 ppm |
| --- | --- |
| CH=CH–N=...–N structure with O–P(=S)(OC$_2$H$_5$)(OC$_2$H$_5$) (known) (B) | 0 |
| CH=CH–N=...–N structure with O–P(=S)(OCH$_3$)(OCH$_3$) (known) (A) | 0 |
| Br–CH=CH–N=...–N structure with O–P(=S)(OCH$_3$)(OC$_3$H$_7$-n) (2) | 100 |
| Cl–CH=CH–N=...–N structure with O–P(=S)(OC$_3$H$_7$-n)(OC$_2$H$_5$) (3) | 100 |
| Cl–CH=CH–N=...–N structure with O–P(=S)(OC$_3$H$_7$-n)(OCH$_3$) (4) | 100 |

EXAMPLE 6

Critical concentration test/soil insects
Test insect: *Tenebrio molitor* - larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all test insects had been killed and was 0% if exactly as many test insects were still alive as in the case of the untreated control.

The active compounds, amounts used and results can be seen from the table which follows:

Table 6

Soil insecticide test
(*Tenebrio molitor* - larvae in the soil)

| Active compound | | Degree of destruction in % at an active compound concentration of 5 ppm |
|---|---|---|
| 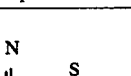 (known) | (B) | 0 |
| 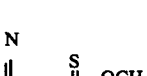 (known) | (A) | 0 |
| 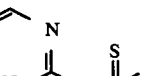 | (1) | 100 |
| 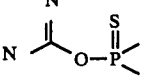 | (2) | 100 |
| 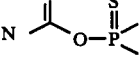 | (4) | 100 |

EXAMPLE 7

Mosquito larvae test
Test insects: Aëdes aegypti - larvae
Solvent: 99 parts by weight
Emulsifier: 1 part by weight benzylhydroxydiphenyl polyglycol ether To produce a suitable preparation of active compound, 2 parts by weight of the active compound were dissolved in 1,000 parts by volume of the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage: 100% means that all the larvae were killed, 0% means that no larvae at all were killed.

The active compounds, the concentrations of the active compounds and the results can be seen from the following table:

Table 7

(Mosquito larvae test)

| Active compound | Active compound concentration of the solution in ppm | Degree of destruction in % |
|---|---|---|
| 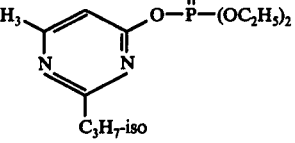 (known) (C) | 1<br>0.1 | 100<br>0 |
| 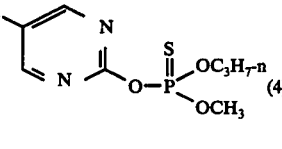 (4) | 1<br>0.1 | 100<br>80 |
| 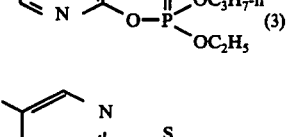 (3) | 1<br>0.1 | 100<br>100 |
| 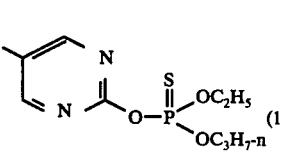 (2) | 1<br>0.1 | 100<br>100 |
| (1) | 1<br>0.1 | 100<br>90 |

EXAMPLE 8

$LD_{100}$ test
Test insects: *Sitophilus granarius*
Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined.

The active compounds, the concentrations of the active compounds, the test insects and the results can be seen from the following table:

Table 8

(LD₁₀₀ test/*Sitophilus granarius*)

| Active compound | | Active compound concentration of the solution in % | Degree of destruction in % |
|---|---|---|---|
| CH₃—[pyrimidine]—O—P(=S)—(OC₂H₅)₂, C₃H₇-iso (known) | | 0.02<br>0.002 | 100<br>0 |
| Cl—[pyrimidine]—O—P(=S)(OC₃H₇-n)(OCH₃) | (C)<br>(4) | 0.002 | 100 |
| Cl—[pyrimidine]—O—P(=S)(OC₃H₇-n)(OC₂H₅) | (3) | 0.002 | 100 |
| Br—[pyrimidine]—O—P(=S)(OCH₃)(OC₃H₇-n) | (2) | 0.002 | 100 |
| Br—[pyrimidine]—O—P(=S)(OC₂H₅)(OC₃H₇-n) | (1) | 0.002 | 100 |

The process of the present invention is illustrated by the following preparative Examples.

EXAMPLE 9 a) 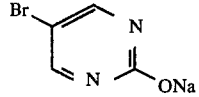

118 g (0.67 mole) of 2-hydroxy-5-bromopyrimidine were added to a solution of 67 g of potassium hydroxide (1.2 moles) in 200 ml of water at room temperature, and the mixture was stirred until all had dissolved. 250 ml of saturated sodium chloride solution were then added to the mixture and the product which had precipitated was filtered off. This gave 95 g (72% of theory) of the sodium salt of 2-hydroxy-5-bromopyrimidine in the form of a colourless powder of melting point >310° C.

b) 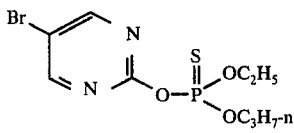 (1)

A mixture of 23.3 g (0.12 mole) of the sodium salt of 2-hydroxy-5-bromopyrimidine, 200 ml of acetonitrile and 20.3 g (0.1 mole) of O-ethyl-O-propylthionophosphoric acid diester chloride was stirred for 48 hours at 50° C. 400 ml of toluene were then added to the reaction mixture, which was washed twice with 300 ml of water at a time. The organic phase was dried over sodium sulfate and freed from the solvent in vacuo. The residue was subjected to slight distillation. This gave 26.5 g (78% of theory) of O-ethyl-O-propyl-O-[5-bromopyrimidin(2)yl]-thionophosphoric acid ester in the form of a light brown oil having a refractive index $n_D^{20}$ of 1.5172.

EXAMPLE 10 a) 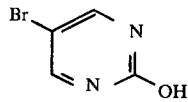

168 g (1.05 moles) of bromine were added dropwise at room temperature to a solution of 132.5 g (1 mole) of 2-hydroxy-pyrimidine hydrochloride in 160 ml of water. The mixture was warmed to 80° C, stirred for a further 15 minutes at this temperature and then cooled to 10° C. The product which had precipitated was filtered off and rinsed with water. This gave 147 g (84% of theory) of 2-hydroxy-5-bromopyrimidine in the form of a pale yellow powder of melting point >250° C.

b) 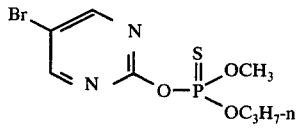 (2)

18.8 g (0.1 mole) of O-methyl-O-propylthionophosphoric acid diester chloride were added dropwise to a suspension of 17.5 g (0.1 mole) of 2-hydroxy-5-bromopyrimidine and 20.7 g (0.15 mole) of potassium carbonate in 300 ml of acetonitrile. The mixture was then stirred for 24 hours at 50° C and washed, after addition of 400 ml of toluene, twice with 300 ml of water at a time; the organic phase was dried over sodium sulfate. The solvent was distilled off in vacuo and the residue was subjected to slight distillation. This gave 15 g (46% of theory) of O-methyl-O-propyl-O-[5-bromopyrimidin(2)yl]-thionophosphoric acid ester in the form of a brown oil having a refractive index $n_D^{26}$ of 1.5306.

EXAMPLE 11

(a) Into a solution as in Example 9a, chlorine gas was slowly bubbled and, upon further processing as there described, the compound

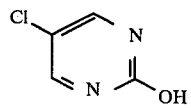

was obtained in 45% yield. Melting point 218° C (with decomposition).

(b) By the process of Example 10b the following compounds were obtained from the product of (a)

above and the appropriate O,O-dialkyl-thionophosphoric acid diester chloride:

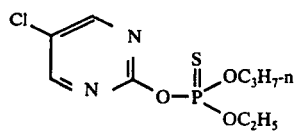

(3) Yield 24% of theory
Refractive index
$n_D^{24}$: 1.5119 and

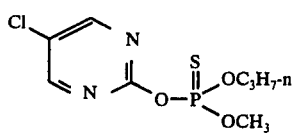

(4) Yield 35% of theory
Refractive index
$n_D^{22}$: 1.5274

It will be appreciated that the instant specification and examples are set forth by way of illustration and not limitation, and that various modifications and changes may be made without departing from the spirit and scope of the present invention.

What is claimed is:

1. An O,O-dialkyl-5-halo-pyrimidin(2)yl-thionophosphoric acid ester of the formula

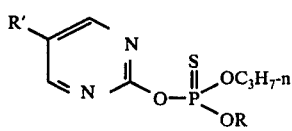

in which
R is methyl or ethyl and
R' is chlorine or bromine.

2. The compound according to claim 1, wherein such compound is O-ethyl-O-propyl-O-[5-bromopyrimidin(2)yl]-thionophosphoric acid ester of the formula

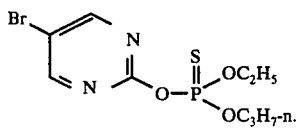

3. The compound according to claim 1, wherein such compound is O-methyl-O-propyl-O-[5-bromopyrimidin(2)yl]-thionophosphoric acid ester of the formula

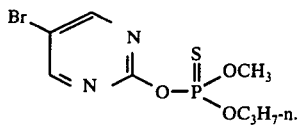

4. The compound according to claim 1, wherein such compound is O-ethyl-O-propyl-O-[5-chloropyrimidin(2)yl]-thionophosphoric acid ester of the formula

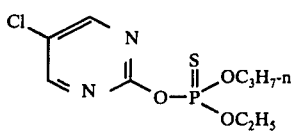

5. The compound according to claim 1, wherein such compound is O-methyl-O-propyl-O-[5-chloropyrimidin(2)yl]-thionophosphoric acid ester of the formula

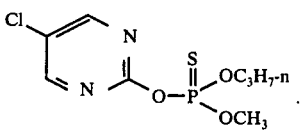

6. An insecticidal or acaricidal composition containing as active ingredient an insecticidally or acaricidally effective amount of a compound according to claim 1 in admixture with a diluent.

7. A method of combatting insects or acarids which comprises applying to the insects or acarids or to a habitat thereof an insecticidally or acaricidally effective amount of a compound according to claim 1.

8. The method according to claim 7 in which said compound is:
O-ethyl-O-propyl-O-[5-bromopyrimidin(2)yl]-thionophosphoric acid ester,
O-methyl-O-propyl-O-[5-bromopyrimidin(2yl]-thionophosphoric acid ester,
O-ethyl-O-propyl-O-[5-chloropyrimidin(2)yl]-thionophosphoric acid ester, or
O-methyl-O-propyl-O-[5-chloropyrimidin(2)yl]-thionophosphoric acid ester.

* * * * *